US006670496B1

(12) United States Patent
Waditschatka

(10) Patent No.: US 6,670,496 B1
(45) Date of Patent: Dec. 30, 2003

(54) PROCESS FOR THE PREPARATION OF PHENYL GLYOXYLIC ACID ESTER OXIMES

(75) Inventor: Rudolf Waditschatka, Gipf-Oberfrick (CH)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/958,715

(22) PCT Filed: Apr. 12, 2000

(86) PCT No.: PCT/EP00/03289

§ 371 (c)(1),
(2), (4) Date: Oct. 10, 2001

(87) PCT Pub. No.: WO00/63162

PCT Pub. Date: Oct. 26, 2000

(30) Foreign Application Priority Data

Apr. 14, 2000 (GB) .............................. 9908530

(51) Int. Cl.$^7$ ............................................ C07C 229/00
(52) U.S. Cl. ....................................................... 560/39
(58) Field of Search .......................................... 560/39

(56) References Cited

U.S. PATENT DOCUMENTS 4,829,085 A    5/1989   Wenderoth et al. ......... 514/522
RE33,989 E    7/1992   Wenderoth et al. ......... 514/522
5,756,426 A    5/1998   Ziegler et al. .............. 504/312
5,981,585 A    11/1999  Ziegler et al. .............. 514/539
6,184,417 B1   2/2001   Kühnle et al. .............. 568/309

FOREIGN PATENT DOCUMENTS

EP    0 629 609    12/1994
EP    0 460 575    9/1996
EP    0 782 982    7/1997

OTHER PUBLICATIONS

Research Disclosure, Oct. 1997, vol. 402, 40221, Method for Preparation of Acetophenone Derivatives.
**W.F. Beech: "Preparation of aromatic aldehydes and ketones from diazonium salts" Journal of The Chemical Society, GB, Chemical Society, Letchworth, 1954, pp. 1297–1302, XP002075827.

Primary Examiner—Amelia Owens
(74) Attorney, Agent, or Firm—Richard E. L. Henderson

(57) ABSTRACT

The invention relates to a process for the preparation of compounds of formula (I) wherein: $R_1$ is optionally substituted alkyl, $R_2$ is $C_1$–$C_6$alkyl, $C_3$–$C_6$cycloalkyl, $C_3$–$C_6$cycloalkyl-$C_1$–$C_2$alkyl, aryl, aryl-$C_1$–$C_2$alkyl, heterocyclyl, heterocycly-$C_1$–$C_2$alkyl, which groups are optionally substituted by alkyl, alkoxy, or halogen; in which process (I) an aniline of formula (II), is diazotized with an organic or inorganic nitrite or nitrous acid; (2) the resulting diazonium salt is reacted with an oxime of formula (III) in presence of a copper(II)-salt.

16 Claims, No Drawings

PROCESS FOR THE PREPARATION OF PHENYL GLYOXYLIC ACID ESTER OXIMES

The invention relates to a process for the preparation of compounds of formula I

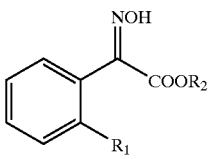

I wherein:

$R_1$ is optionally substituted alkyl, $R_2$ is $C_1$–$C_6$alkyl, $C_3$–$C_6$cycloalkyl, $C_3$–$C_6$cycloalkyl-$C_1$–$C_2$alkyl, aryl, aryl-$C_1$–$C_2$alkyl, heterocyclyl, heterocyclyl-$C_1$–$C_2$alkyl, which groups are optionally substituted by alkyl, alkoxy, or halogen; in which process (1) an aniline of formula II,

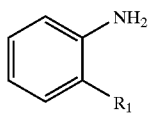

II wherein $R_1$ is as defined for formula I, is diazotized with an organic or inorganic nitrite or nitrous acid;

(2) the resulting diazonium salt is reacted with an oxime of formula III

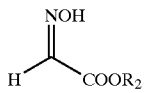

III wherein $R_2$ is as defined for formula I, in presence of a copper(II)-salt.

The compounds of formula I are intermediates for the preparation of pesticides; e.g. EP-A-460575 and WO 95/18789.

Several processes for preparing compounds of formula I are known, which, however, are not always satisfying in any respect, as number of reaction steps, yields, availability of educts, safety and ecology. For example EP-A-253213 discloses a process comprising a Grignard reaction; in EP-A-782982 a reaction with a lithium organic reagent, as butyllithium, is described.

These processes are not suitable for large scale production, as organometallic reactions have serious disadvantages with respect to economic, ecological and safety reasons. Other methods for preparation of compounds of formula I are therefore highly desirable.

Reactions of phenyl diazonium salts with oximes are known, e.g. J. Chem. Soc. 1954, p.1297–1302; Research Disclosure, October 1997, Vol. 402, 40221 and WO 98/50335. Reactions with glyoxylic acid oxime derivatives are not disclosed in these references.

Surprisingly, it has been found that compounds of formula I may be obtained directly from the corresponding anilines by reaction with a glyoxylic acid oxime derivative in yields of up to 80% and in good qualities. The method provided herewith is distinguished by ready availability of the raw materials, good technical feasibility and is economically and ecologically favorable.

An additional advantage of the reaction according to the invention is that compounds of formula I are obtained almost exclusively in form of their E-isomers with respect to the oxime double bond (E:Z>95:5), which isomer is biologically more active than the Z-isomer in the corresponding final active ingredients. A separate isomerisation or isomer-purification step can therefore be avoided.

Alkyl groups are straight-chain or branched and will typically be methyl, ethyl, n-propyl, isopropyl, n-butyl, sec-butyl, isobutyl, tert-butyl, n-amyl, tert-amyl, 1-hexyl or 3-hexyl. Halogen and halo substituents are fluoro, chloro, bromo or iodo. Alkoxy is typically methoxy, ethoxy, propyloxy, isopropyloxy, n-butyloxy, isobutyloxy, sec-butyloxy and tert-butyloxy. Methoxy and ethoxy are preferred. Cycloalkyl is cyclopropyl, cyclobutyl, cyclopentyl, or cyclohexyl. Aryl is phenyl or naphthyl; phenyl is preferred. Heterocycl stands for aromatic and non-aromatic cyclic moieties with 3 to 8 ring members of which at least one is a nitrogen, oxygen or sulfur. Heterocycl typically encompasses up to three heteroatoms where preferably at least one is nitrogen. Typical examples of heterocycl are aromatic moieties like furyl, benzofuranyl, thienyl, benzothienyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, isoindolyl, triazinyl, and the like; and non-aromatic moieties like tetrahydrofuranyl, pyrazolidinyl, pyrrolidinyl, pyrrolinyl, imidazolinydinyl, piperidinyl, pyranyl, thiopyranyl, piperazinyl, morpholinyl, thiomorpholinyl, and the like.

$R_1$ is optionally substituted alkyl, wherein the substituents have to be inert towards the reactions; suitable substituents are for example halogen, alkoxy and phenoxy. $R_2$ is preferably $C_1$–$C_4$alkyl, most preferably ethyl or methyl.

The reaction according to the invention is particularly suitable for the preparation of compounds of formula I, wherein $R_1$ is methyl. In this case, the important intermediates of formula V.1 for the preparation of pesticides of formula VI may be prepared according to the following reaction scheme:

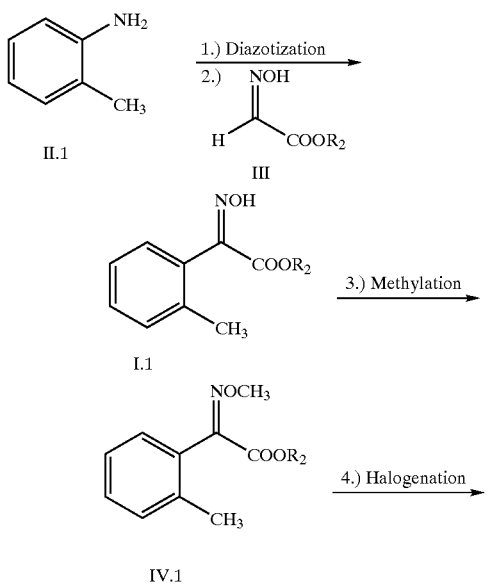

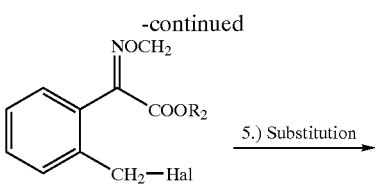

V.1

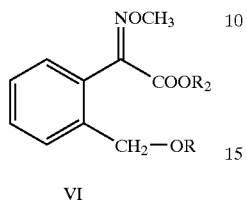

VI

This reaction sequence and parts of it are also objects of the present invention. R represents an organic radical linked via an oxygen bridge. It encompasses the designations as e.g. disclosed in EP-A-460575 and WO 95/18789, but is not limited to such examples.

Due to its relative instability, the oxime of formula III is advantageously prepared immediately before use by reaction of the corresponding glyoxylic acid ester IIIA or its hemiacetal IIIB

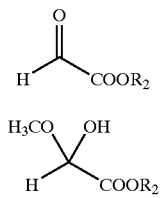

with hydroxylamine or a salt thereof, as the hydrochloride, the sulfate, the phosphate or the acetate, in aqueous solution and further reacted without isolating. Compounds of formulae II, III, IIIA and IIIB are well known in the art and are partially commercially available.

The diazotation reaction is carried out in an organic solvent with an organic nitrite, e.g. an alkyl nitrite as isoamyl nitrite, or an aryl nitrite, as phenyl nitrite; or, more preferably, in aqueous solution with nitrous acid or a salt thereof, in presence of an acid. Preferred nitrites are sodium nitrite, potassium nitrite, magnesium nitrite, particularly preferred is sodium nitrite. Preferred acids are hydrochloric acid, sulfuric acid and nitrosulfuric acid; particularly preferred is sulfuric acid. Advantageous is a temperature of −10 to +30° C. and a pH 0–3.

The diazonium salt is preferably reacted in the presence of a copper(II)-salt like copper acetate, $CuCl_2$ or $CuSO_4$ at −10 to +40° C., more preferably −10 to +15° C., and at pH 2–7, more preferably at pH 3–5. The amount of the copper(II)-salt is 1 to 30 mol %, more preferably 5 to 20 mol %, in relation to the aniline of formula II. The addition of a reducing agent, as a sulfite salt, e.g. sodium sulfite or potassium sulfite, may be advantageous, preferably in amounts of 1 to 20 mol %, more preferably 5 to 10 mol %, in relation to the aniline of formula II.

In a preferred mode of running the reaction step (2), an aqueous suspension of the diazonium salt is added to an aqueous solution comprising the aldoxime of formula III, the copper(II)-salt and optionally the reducing agent, maintaining a pH of 3–5 by simultaneously adding a base to the reaction mixture. It may be advantageous for working up and purification of intermediates and products to run the reaction steps (1) and (2) in presence of a hydrophobic solvent, as hydrocarbons, halogenated hydrocarbons, ethers and ketones, for example hexane, cyclohexane, methylcyclohexane, benzene, toluene, xylene, mineral oil, kerosene, methylene chloride, chloroform, ethylenechloride, chlorobenzene and dichlorobenzene.

Methylation of the oxime group is carried out for example with methyl iodide, methyl bromide, methyl chloride or dimethyl sulfate in a solvent, preferably in presence of a base.

Methods for halogenation include iodination with $I_2$, bromination with NBS (N-bromo-succinimide) or $Br_2$, chlorination with NCS (N-chlorsuccinimide) or $Cl_2$ or $SO_2Cl_2$. Particularly preferred is the bromination with NBS.

Suitable solvents are halogenated hydrocarbons, typically chlorobenzene, bromobenzene, chloroform, dichloromethane, trichloromethane, dichloroethane or trichloroethane; ethers, typically diethyl ether, tert-butylmethyl ether, glyme, diglyme, tetrahydrofuran or dioxane, as well as nitrogen containing compounds like triethylamine, piperidine, pyridine, alkylated pyridine, quinoline and isoquinoline.

The compound of formula V may be reacted with a compound of the formula HOR, wherein R is an organic radical, under basic conditions in a solvent according to known methods, to obtain the active ingredients of formula VI, which may, if desired, be transesterified or amidated according to generally known methods.

PREPARATION EXAMPLES (a) Preparation of 2-methyl benzene diazonium salt (solution A): To an ice-cooled mixture of 225 g water, 35.1 g concentrated sulfuric acid (0.36 mol) and 32.0 g 2-toluidine (0.30 mol), an aqueous solution of 21.0 g sodium nitrite (0.303 mol) in 80 g water is added at 0–5° C. The mixture is stirred for ca. 15 minutes, and the excess sodium nitrite is destroyed with 0.9 g sulfamic acid.

(b) Preparation of glyoxylic acid methylester oxime (solution B): In a separate reactor 54.0 g glyoxylic acid methylester methylhemiacetal (0.45 mol), 150 g water, 27.0 g glacial acetic acid (0.45 mol) and 29.7 g aqueous hydroxylamine 50% (0.45 mol) are mixed for ca. 30 minutes at 0–5° C.; subsequently 15.0 g solid copper (II)sulfate (0.06 mol) and 3.78 g of sodium sulfite (0.03 mol) are added in one portion.

(c) Preparation of 2-methylphenyl glyoxylic acid methylester oxime: Solution A is added to solution B at 12–18° C., maintaining the pH at 3–4 by addition of a 20% aqueous solution of sodium acetate. During the reaction a constant stream of nitrogen is evolved and the product is crystallizing from the aqueous medium. The mixture is stirred for 2 hours at ca. 20° C., the suspension is filtered and the product is washed with water and dried at 50° C. under vacuum to yield 42.8 g dark crystals, m.p. 92° C. (decomposition). $^1$H-NMR (CDCl$_3$): 2.18 and 3.78 ppm (2 methyl groups); exclusively E-isomer (71% of theory).

What is claimed is:

1. A process for the preparation of a compound of formula I

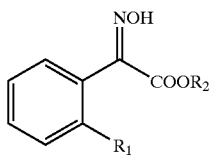

wherein:

$R_1$ is optionally substituted alkyl, $R_2$ is $C_1$–$C_6$alkyl, $C_3$–$C_6$cycloalkyl, $C_3$–$C_6$cycloalkyl-$C_1$–$C_2$alkyl, aryl, aryl-$C_1$–$C_2$alkyl heterocyclyl, heterocyclyl-$C_1$–$C_2$alkyl, which groups are optionally substituted by alkyl, alkoxy and halogen, comprising the steps of:

(1) diazotizing an aniline of formula II

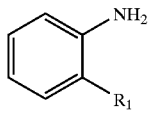

wherein $R_1$ is as defined for formula I, with an organic or inorganic nitrite or nitrous acid;

(2) reacting the resulting diazonium salt with an oxime of formula III

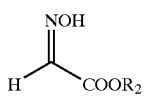

wherein $R_2$ is as defined for formula I, in presence of a copper(II)-salt.

2. A process according to claim 1, wherein the copper (II)-salt is $CuCl_2$ or $CuSO_4$.

3. A process according to claim 1, wherein the amount of the copper(II)-salt is 1 to 30 mol %, in relation to the compound of formula II.

4. A process according to claim 1, wherein the step of reacting the diazonium salt with an oxime occurs in the presence of a reducing agent.

5. A process according to claim 4, wherein the reducing agent is sodium sulfite or potassium sulfite.

6. A process according to claim 1, wherein in formulae I, II and III $R_1$ is methyl and $R_2$ is methyl or ethyl.

7. A process for the preparation of a compound of formula V.1, comprising the steps set forth below:

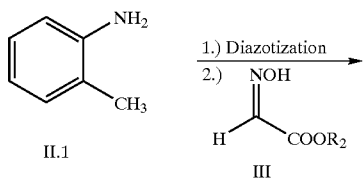

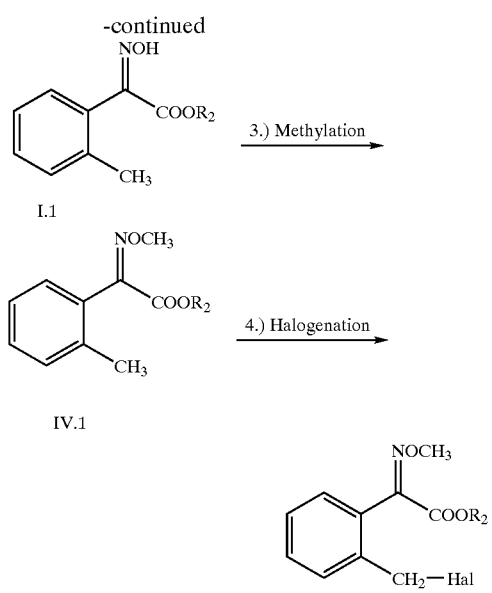

wherein $R_2$ is $C_1$–$C_6$alkyl, $C_3$–$C_6$cycloalkyl, $C_3$–$C_6$cycloalkyl-$C_1$–$C_2$alkyl, aryl, aryl-$C_1$–$C_2$alkyl, heterocyclyl, heterocyclyl-$C_1$–$C_2$alkyl, which groups are optionally substituted by alkyl, alkoxy and halogen, and further wherein the aniline of formula II.1 is diazotized with an organic or inorganic nitrite or nitrous acid; and the resulting diazonium salt is reacted with an oxime of formula III, wherein $R_2$ is as defined for formula I.1, in presence of a copper(II)-salt.

8. A process according to claim 1, wherein $R_1$ is an unsubstituted or halogen-, phenoxy-, methoxy-, ethoxy-, propyloxy-, isopropyloxy-, n-butyloxy-, isobutyloxy-, sec-butyloxy- or tert-butyloxy-substituted methyl, ethyl, n-propyl, isopropyl, n-butyl, sec-butyl, isobutyl, tert-butyl, n-amyl, tert-amyl, 1-hexyl or 3-hexyl.

9. A process according to claim 1, wherein $R_2$ is a $C_1$–$C_4$ alkyl.

10. A process according to claim 1, wherein the heterocyclyl is an aromatic and non-aromatic heterocylcyl moiety with 3 to 8 ring members of which at least one is a nitrogen, oxygen or sulfur.

11. A process according to claim 10, wherein the heterocyclyl is furyl, benzofuranyl, thienyl, benzothienyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, isoindolyl, triazinyl, tetrahydrofuranyl, pyrazolidinyl, pyrrolidinyl, pyrrolinyl, imidazolinydinyl, piperidinyl, pyranyl, thiopyranyl, piperazinyl, morpholinyl or thiomorpholinyl.

12. A process according to claim 1, wherein $R_2$ is an unsubstituted or halo gen-, methoxy-, ethoxy-, propyloxy-, isopropyloxy-, n-butyloxy-, isobutyloxy-, sec-butyloxy- or tert-butyloxy-, methyl-, ethyl-, n-propyl-, isopropyl-, n-butyl-, sec-butyl-, isobutyl-, tert-butyl-, n-amyl-, tert-amyl-, 1-hexyl- or 3-hexyl-substituted $C_1$–$C_6$alkyl, $C_3$–$C_6$cycloalkyl, $C_3$–$C_6$cycloalkyl-$C_1$–$C_2$alkyl, aryl, aryl-$C_1$–$C_2$alkyl, heterocyclyl or heterocyclyl-$C_1$–$C_2$alkyl.

13. A process according to claim 12, wherein the heterocyclyl is an aromatic and non-aromatic heterocylcyl moiety with 3 to 8 ring members of which at least one is a nitrogen, oxygen or sulfur.

14. A process according to claim 13, wherein the heterocyclyl is furyl, benzofuranyl, thienyl, benzothienyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, isoindolyl, triazinyl, tetrahydrofuranyl, pyrazolidinyl, pyrrolidinyl, pyrrolinyl, imidazolinydinyl, piperidinyl, pyranyl, thiopyranyl, piperazinyl, morpholinyl or thiomorpholinyl.

15. A process according to claim 1, wherein the step of diazotizing the aniline of formulae is performed with a compound selected from the group consisting of isoamyl nitrite, phenyl nitrite, nitrous acid, sodium nitrite, potassium nitrite, and magnesium nitrite.

16. A process for the preparation of a compound of formula I

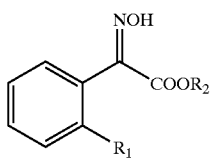

wherein:
   $R_1$ is an unsubstituted or halogen-, phenoxy-, methoxy-, ethoxy-, propyloxy-, isopropyloxy-, n-butyloxy-, isobutyloxy-, sec-butyloxy- or tert-butyloxy-substituted methyl, ethyl, n-propyl, isopropyl, n-butyl, sec-butyl, isobutyl, tert-butyl, n-amyl, tert-amyl, 1-hexyl or 3-hexyl; and
   $R_2$ is an unsubstituted or halogen-, methoxy-, ethoxy-, propyloxy-, isopropyloxy-, n-butyloxy-, isobutyloxy-, sec-butyloxy- or tert-butyloxy-, methyl-, ethyl-, n-propyl-, isopropyl-, n-butyl-, sec-butyl-, isobutyl-, tert-butyl-, n-amyl-, tert-amyl-, 1-hexyl- or 3-hexyl-substituted $C_1$–$C_6$ alkyl, $C_3$–$C_6$ cycloalkyl, $C_3$–$C_6$ cycloalkyl-$C_1$–$C_2$ alkyl, aryl, aryl-$C_1$–$C_2$ alkyl, heterocyclyl or heterocyclyl-$C_1$–$C_2$ alkyl; wherein the heterocyclyl is an aromatic and non-aromatic heterocylcyl moiety with 3 to 8 ring members of which at least one is a nitrogen, oxygen or sulfur; comprising the steps of:

(1) diazotizing an aniline of formula II with a compound selected from organic nitrites, inorganic nitrites and nitrous acid to obtain a diazonium salt;

(2) preparing an oxime of formula III by reacting hydroxylamine or a salt of hydroxylamine with a glyoxylic acid ester of formula IIIA or an hemiacetal of formula IIIB (3) reacting the diazonium salt with the oxime in presence of a copper(II)-salt.

* * * * *